United States Patent [19]

Buzzard et al.

[11] Patent Number: 5,570,704

[45] Date of Patent: Nov. 5, 1996

[54] UNIVERSAL, USER-ADJUSTABLE ORAL CAVITY APPLIANCE TO CONTROL SNORING AND REDUCE EPISODES OF OBSTRUCTIVE SLEEP APNEA

[75] Inventors: Ronald D. Buzzard, Pittsburg, Kans.;
Larry D. Buzzard, Grove, Okla.;
Peggy L. Kenyon, Pittsburg, Kans.;
Brian T. Agre, Tulsa, Okla.

[73] Assignee: Snoreless Corp, Pittsburg, Kans.

[21] Appl. No.: 359,881

[22] Filed: Dec. 20, 1994

Related U.S. Application Data

[63] Continuation-in-part of Ser. No. 144,652, Oct. 28, 1993, abandoned.

[51] Int. Cl.$^6$ ..................................................... A61F 5/56
[52] U.S. Cl. ..................................................... 128/848
[58] Field of Search .......................... 128/848, 859–862; 433/6, 7, 140

[56] References Cited

U.S. PATENT DOCUMENTS

| | | |
|---|---|---|
| 2,705,492 | 4/1955 | Chandler . |
| 2,966,908 | 1/1961 | Cathcart . |
| 3,132,647 | 4/1962 | Corniello . |
| 3,217,708 | 7/1963 | Roberts . |
| 3,224,443 | 12/1965 | Monaghan . |
| 3,277,892 | 1/1966 | Tepper . |
| 3,333,582 | 8/1967 | Cathcart . |
| 3,434,470 | 3/1969 | Strickland . |
| 3,536,069 | 9/1969 | Gores . |
| 4,305,709 | 12/1981 | Bruhn et al. . |
| 4,396,373 | 8/1983 | Dillinger .............................. 433/6 X |
| 4,519,386 | 5/1985 | Sullivan ................................ 128/859 |
| 4,553,549 | 11/1985 | Pope et al. . |
| 4,637,796 | 1/1987 | Korn ...................................... 433/7 |
| 4,715,368 | 12/1987 | George . |
| 4,898,535 | 2/1990 | Bergersen . |
| 4,901,737 | 2/1990 | Toone . |
| 4,969,822 | 11/1990 | Summer . |
| 5,018,533 | 5/1991 | Hawkins .............................. 128/848 |
| 5,056,534 | 10/1991 | Wright . |
| 5,117,816 | 6/1992 | Shapiro et al. . |
| 5,174,284 | 12/1992 | Jackson . |
| 5,267,862 | 12/1993 | Parker . |
| 5,347,996 | 9/1994 | Huan .................................. 128/859 X |
| 5,365,945 | 11/1994 | Halstrom ............................ 128/859 X |
| 5,409,017 | 4/1995 | Lowe ................................. 128/859 X |

FOREIGN PATENT DOCUMENTS

| | | |
|---|---|---|
| 0254918 | 7/1987 | European Pat. Off. . |
| 374163 | 7/1921 | Germany . |

OTHER PUBLICATIONS

Cartwright & Samelson, "The Effects of a Nonsurgical Treatment for Obstructive Sleep Apnea—The Tongue-Retaining Device", JAMA, Aug. 13, 1982 —Vol. 248, No. 6 (pp. 705–709).

Harman, Wynne, Block, "The Effect of Weight Loss on Sleep-Disordered Breathing and Oxygen Desaturation in Morbidly Obese Men", CHEST, Sep. 1982—vol. 3 (pp. 291–293).

Sullivan, Berthon-Jones, Issa, Eves, "Reversal of Obstructive Sleep Apnoea by Continuous Positive Airway Pressure Applied Through the Nares", The Lancet, Apr. 18, 1981 (pp. 862–865).

James L. Mosley, "Snore No More!", 1990.

"Stalking a Good Night's Sleep", Consumer Reports, Mar. 1987 (pp. 136–138).

The Charolett Observer, Oct. 18, 1989 A Raveled Night's Sleep No More: Snoring Can Be Cured.

Reprinted from the Journal of Clinical Ortohdontics, Ernest A. Rider, DDS, Removable Herbst Appliance for Treatement of Obstructive Sleep Apnea.

Reader's Digest, condensed from Old Farmer's Almanac, Jim Collins, Snore No More.

Dallas Daily Morning News, *Device helps snorers, spouses sleep soundly,* Mar. 7, 1994.

May 1993 letter re Herbst Appliance from Charles L. Oakes, D.D.S., Inc., Specialist in Orthodontics, Member of the Southern Sleep Society.

Nov. 9, 1992 letter to Dr. Charles Oakes from Mr. Michael E. Reeder, regarding the Herbst Appliance.

Aug. 12, 1992 letter to Dr. Charles Oakes from Kathleen Pharr regarding the Herst Appliance.

Chapter 69, pp. 722–735, Dental Appliances for The Treatment of Snoring and Obstructive Sleep Apnea, Alan A. Lowe.

*Primary Examiner*—Jessica J. Harrison
*Assistant Examiner*—Michael O'Neill
*Attorney, Agent, or Firm*—Head, Johnson & Kachigian

[57] ABSTRACT

A universal, user-adjustable oral cavity appliance is provided for maintaining the mandible in an open and forward position during sleep. The appliance includes a lingual mandibular retaining strap adapted to contact and imbed in the lingual mandibular tissues below the mandibular anterior teeth and a labial maxillary retaining strap adapted to contact and imbed in the labial maxillary tissues above the maxillary anterior teeth. The retaining straps are adjustably connected such that the relative position of each strap to the other may be varied to obtain a separation between the maxilla and mandible and a forward thrust of the mandible sufficient to prevent the occlusion of the oropharyngeal airway.

22 Claims, 3 Drawing Sheets

UNIVERSAL, USER-ADJUSTABLE ORAL CAVITY APPLIANCE TO CONTROL SNORING AND REDUCE EPISODES OF OBSTRUCTIVE SLEEP APNEA

CROSS REFERENCE TO RELATED APPLICATION

This is a continuation-in-part of United States patent application Ser. No. 08/144,652, filed Oct. 28, 1993, that is now abandon.

BACKGROUND OF THE INVENTION

In an article in the April 1993 issue of the New England Journal of Medicine it is estimated that 97 million Americans habitually snore. Of these, some 16 million are thought to be afflicted with sleep apnea. Sleep apnea is a condition in which there is a complete cessation of breathing during rest.

Snoring itself, absent apneic episodes, is destructive. Obvious is the effect of snoring on the spouse or mate of the snorer. Restless, intermittent sleep patterns caused by a spouse's snoring binges serve to breed resentment in relationships and produce daytime irritability and sleepiness. Marital problems may extend into the sexual arena, where this part of the relationship becomes strained after decisions are made to sleep in separate bedrooms, limit travel or family outings, and otherwise avoid partners in situations where their snoring would be troublesome or embarrassing.

Sleep-induced apnea compounds the problems associated with snoring. There are two forms of sleep apnea. In one form, breathing is halted when the respiratory muscles temporarily cease to function. But the most common form of sleep apnea, called obstructive apnea, arises from a blockage of the oropharyngeal airway. With either form, increasing levels of carbon dioxide in the blood ultimately triggers a resumption in respiration, usually accompanied by gasping, wheezing breaths. The snorer is momentarily awakened at the conclusion of the apneic episode, only to fall almost immediately back to sleep to then repeat the cycle.

Besides the effects associated with mere snoring, persons with sleep apnea are likely to suffer additional personal and economic harms. In critical cases, sleep apnea can contribute to cardiac arrhythmia and even death, and as a consequence of the numerous nightly sleep disruptions, of which the snorer may not even be consciously aware, those with sleep apnea may experience severe daytime drowsiness which may lead to accidents and injuries. This chronic sleepiness translates into economic harm through poor job performance. Persons with sleep apnea are more apt to be late to work and distracted during working hours. They take more sick leave, and usually give less attention to detail.

Obstructive sleep apnea largely afflicts overweight men, although it can effect men and women of any stature. During sleep, tissues in the mouth and throat, which may have become weakened, enlarged, or flabby, relax causing the airway to become occluded, thus inducing the apneic episode. Only when the amount of carbon dioxide in the blood rises to a level sufficient to provoke the breathing center of the brain, does normal respiration resume. As stated above, in severe cases, death may result.

Many approaches have been taken in addressing the problem of snoring and sleep apnea, ranging from simple weight loss, which has been shown to somewhat reduce snoring and apneic episodes in overweight persons, to the use of continuous positive air pressure applied through the nares, to radical surgical approaches such as tracheostomy and uvulopalatopharyngoplasty. But by far the most widely used, and most extensively developed, approach includes the utilization of various oral cavity devices designed to, in differing manners, reduce or eliminate snoring and, consequently, sleep-induced apneic events.

Of the oral cavity appliances, some, such as U.S. Pat. Nos. 3,434,470 and 5,056,534 function to control the amount of air capable of being moved through the mouth, either lessening the intake volume of air to an extent wherein the person is incapable of producing a snore, or shutting off completely the passage of air through the mouth unless the jaw is opened to a degree sufficient to prohibit oropharyngeal occlusion. Other types of devices, such as U.S. Pat. Nos. 3,132,647 and 4,715,368, operate by physically depressing and constraining the tongue of the wearer to prevent occlusion of the airway. Still others, examples of which are U.S. Pat. Nos. 4,304,227 and 4,676,240, act to maintain an open airway by retaining the tongue in a position extending forward of the teeth.

The problems with these apparatuses are obvious. Any prevention or restriction of airflow through the mouth is not an option for persons with allergies or other conditions which limit the volume of air that can be breathed through the nasal passages. And, as is readily imaginable, the devices functioning to depress the tongue also function to cause gagging, and are too uncomfortable for most. Further, as most people are not accustomed to sleeping with their tongue stretched outside their mouth, the tongue retention devices are awkward and their appearance startling.

The more successful oral cavity appliances are those that serve to set the mandible in an open and forward position relative to the normal posture of the jaw during sleep. U.S. Pat. No. 4,901,737 discloses such a device. The appliance of the '737 patent comprises a rigid, acrylic V-shaped wedge molded to the entire mandibular dentition and a portion of the maxillary dentition. The mandibular incisal (cutting) edge is embedded from cuspid to cuspid, with a lip extending over the labial (toward the lip) surface of the mandibular incisors. The occlusal (contacting) surfaces and lingual (toward the tongue) cusps of all mandibular teeth are embedded, with the appliance extending over the lingual surfaces and extending downwardly into the lingual vestibule. Crosswise palatal stiffening is provided by heavy dental wire, and clips or clasps are used at the first maxillary molars to snap on to the teeth. A labial arch wire fits over and extends between the maxillary canines in an attempt to avoid splaying of the teeth, and a cingulum arch wire is provided to try and prevent eruption of the maxillary canines.

In U.S. Pat. No. 5,117,816 another type of device is shown. This thermoplastic implement substantially covers the entire maxillary dentition and has a lower surface portion which includes a downwardly extending flange intended to extend into the lingual vestibule of a user in order to maintain a forward posture of the lower jaw. An airway passage is centrally located to allegedly permit adequate breathing through the mouthpiece if nasal blockage is present.

The main problem with both of these devices is the pressure applied to the teeth of the user. Both appliances use the teeth to a significant degree to obtain the open and extended position of the mandible. The device of the '737 patent receivingly engages the mandibular incisors to cause the mandible to protrude forward, whereas the downwardly extending flange of the '816 patent apparatus serves to maintain the forward position of the mandible by similarly contacting the rear of a user's lower front teeth. Besides the general discomfort caused by the stressing of the teeth, permanent repositioning of the teeth may occur if undue pressure is applied for too long a duration. Another problem common to both appliances is that they can only be used in connection with the presence of dentition, either natural or prosthetic.

Other problems with the device of the '737 patent include the time and cost associated with its fitting and manufacture. The fitting and manufacture of the device can only be accomplished by a professional, and quickly becomes comparatively expensive. Time is spent by the professional in determining through trial and error the appropriate fit for the user. Then, molds are taken of the maxillary and mandibular dentition, and such molds are mounted in the recorded position for the formation of a template. The appliance is then cast of a heat curable plastic (acrylic) with the crosswires and arch wires embedded in the casting material.

The device also covers the entire mandibular dentition and includes a continuous semicircular lingual flange which extends downwardly into the lingual vestibule giving an unusual and cramped feel to the tongue. Further, the presence of crosswires and arch wires invites manipulation by the tongue which may lead to tongue sensitivity or other soreness. Further, as it is made of a hard plastic, the device is unyielding as far as allowing slight movement for swallowing or allowing the stretching or working of the jaw muscles.

The apparatus of the '816 patent, while made of a thermoplastic material, consists of an upper surface portion only that substantially covers the entire maxillary dentition with a lower surface portion extending downwardly into the lingual vestibule. Stabilization of the mandible in the forward position is supposedly effected by the position of the downward flange. The degree of stabilization which can be maintained, however, necessarily varies to the degree the mandible is opened or closed by the user. As the user's mouth opens and closes to any extent, the flange will ride up and down the lingual side of the lower front teeth. Further, while the device does contain an airway passage, the passage is surrounded by a concave portion on the rear face of the flange to provide a space for forward positioning of the tongue. But this forward positioning of the tongue will block the air passage forcing the user to breath through the nares.

SUMMARY OF THE INVENTION

It is therefore an object of this invention to overcome the limitations of the prior art by providing an improved apparatus that reduces snoring and apneic episodes caused by obstructive sleep-induced apnea by maintaining the mandible of the user in an open and forward position. Specifically, the present invention comprises an oral cavity apparatus that functions to maintain the open and forward posture of the mandible during sleep by repositioning and stabilizing the maxilla and mandible of the user without applying pressure to the user's teeth.

It is also an object of the invention to provide an improved oral cavity device that can be used by persons with no natural dentition or prosthetic dentition to give relief from snoring and sleep apnea, and that provides for breathing through the mouth, nares or both.

It is a further object of the invention to supply an anti-snore device made from a thermoplastic material, or other resilient, semi-rigid plastic derivative or substance, which is universal in fit and is usable by consumers in an over-the-counter manner, without professional assistance, and which includes for the consumer a means of adjusting the degree of separation to be maintained between the maxilla and mandible and of adjusting the degree to which the mandible is moved forward.

Another object is to provide a universal, user-adjustable oral cavity appliance which is comfortable, inexpensive and easy to understand and use.

It is a still further object of the invention to provide an oral cavity device that does not cover either the entire maxillary or mandibular dentition and, hence, is aesthetically pleasing.

These and other objects are achieved by providing a universal oral cavity appliance adjustable to fit the structure of the mouth which functions to maintain the mouth in an open position and the mandible extended in a forward posture by appropriately arranging and stabilizing the maxilla and mandible. The device comprises a lingual mandibular retaining strap adapted to contact and imbed in the lingual mandibular tissues below the mandibular anterior teeth. A labial maxillary retaining strap is also provided, it being adapted to contact and imbed in the labial maxillary tissues above the maxillary anterior teeth. A means is provided for adjustably connecting the straps such that the relative position of each strap to the other may be varied to obtain a separation between the maxilla and mandible and a forward thrust of the mandible sufficient to prevent a occlusion of the oropharyngeal airway during sleep.

A better understanding of the invention, and the objects thereof, will be obtained from the following description, taken in conjunction with the attached drawings.

BRIEF DESCRIPTION OF THE DRAWINGS

FIG. 4 is a sectional view taken along the line 4—4 of FIG. 1a.

DETAILED DESCRIPTION OF THE PREFERRED EMBODIMENT

Figure 1:
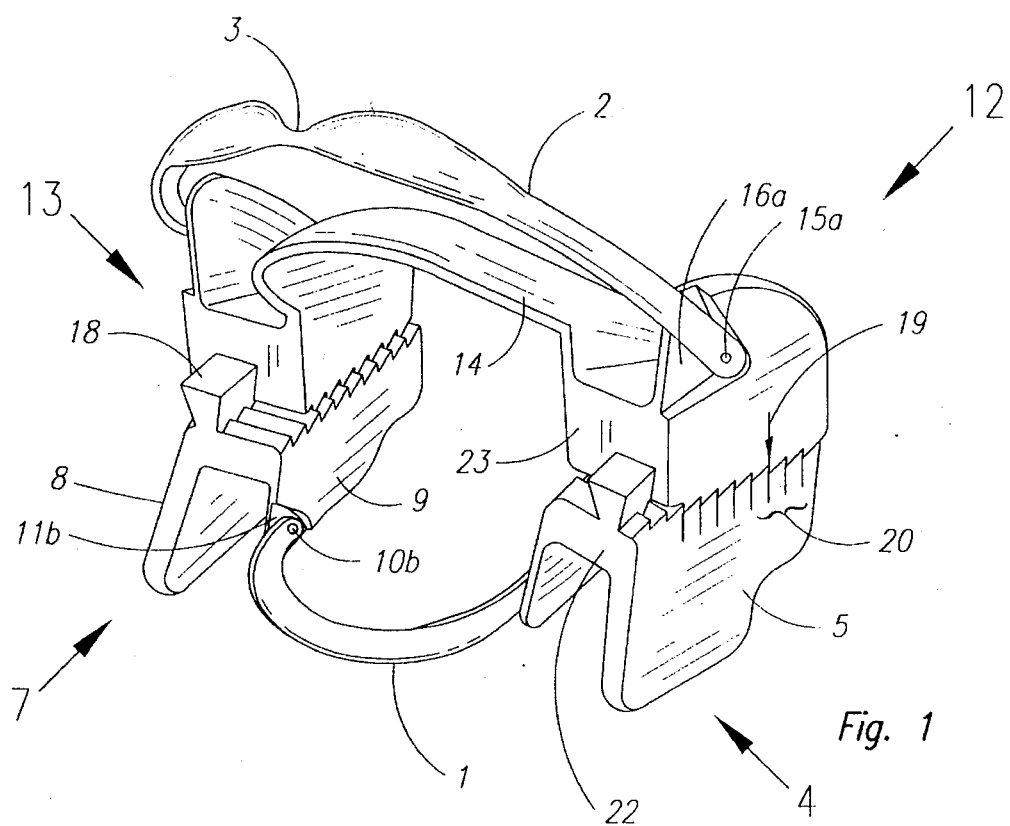
FIG. 1 is a three-quarter perspective view of the preferred embodiment of the invention from above and to the left side of the invention.
Figure 1A:
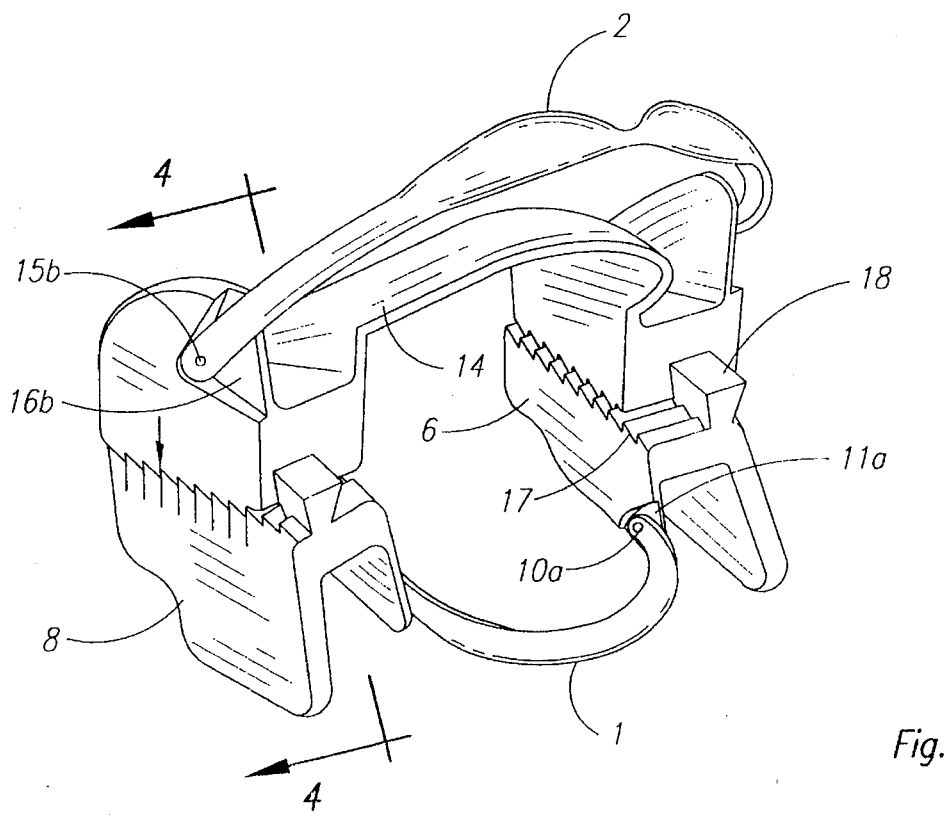
FIG. 1a is a three-quarter perspective view of the preferred embodiment of the invention from above and to the right side of the invention.

Referring to FIGS. 1 and 1a, a universal, user-adjustable oral cavity appliance is provided for maintaining the mandible in an open and forward position during sleep. The device includes a lingual mandibular retaining strap 1, which is adapted to contact and imbed in the lingual mandibular tissues below the mandibular anterior teeth. Mandibular anterior teeth as used herein means those teeth anterior to the mandibular bicuspids. A labial maxillary retaining strap 2 is adapted to contact and imbed in the labial maxillary tissues above the maxillary anterior teeth. As used herein, the maxillary anterior teeth refers to those teeth anterior to the maxillary bicuspids. Retaining straps 1, 2 are preferably of an elliptical cross-section, with the labial maxillary retaining strap 2 being provided with a frenulum notch 3.

A means is provided for adjustably connecting retaining straps 1, 2 such that the relative position of each strap to the other may be varied to obtain a separation between the user's maxilla and mandible and a forward thrust of the mandible sufficient to prevent occlusion of the oropharyngeal airway. Labial maxillary retaining strap 2 pulls against the maxillary tissue in reaction to lingual mandibular retaining strap 1 pushing against the mandibular tissues. Since the labial maxillary retaining strap 2 pulls against the mandibular tissues and the lingual mandibular retaining strap 1 pushes against the mandibular tissues, each applying pressure to the mandibular tissues, said retaining straps may alternatively be referred to as pressure straps. The pressure exerted by the pulling and pushing forces cause a forward thrust of the mandible. The means provided for adjustably connecting retaining straps 1, 2 is of a construction as to also provide a separation between the maxilla and mandible.

In Applicant's preferred embodiment, the means for adjustably connecting retaining straps 1, 2 includes the use of a lower pair of U-shaped members 4, 7, otherwise referred to as mandibular blocks or lower pieces. The left lower U-shaped member 4 has two side walls, a buccal side wall 5 and a lingual side wall 6. The right lower U-shaped member 7, likewise has a buccal side wall 8 and a lingual side wall 9. The side walls of both lower U-shaped members 4, 7 are connected by a horizontal portion 22 having thereon a series of upwardly disposed one-way ramped ridges 17, as well as dove-tailed keys 18 which are superimposed upon, or integrated with, the one-way ramped ridges 17. Preferably, ridges 17 are spaced one millimeter apart to allow for incremental adjustment.

The heretofore described structure as combined can also be said to comprise the lower piece of a two-piece universal, user-adjustable oral cavity appliance. As further shown in FIGS. 1 and 1a, lingual mandibular retaining strap 1 is preferably connected to lower U-shaped members 4 and 7 by hole and peg assemblies. As shown in FIG. 1, lingual mandibular retaining strap 1 is connected by hole and peg assembly 10b to the anterior portion of lingual side wall 9 of right lower U-shaped member 7. There is provided at this juncture a clearance 11b which allows lingual mandibular retaining strap 1 to move slightly while maintaining its imbedded level in the lingual mandibular tissues and allows for universal fit. Similarly, FIG. 1a shows the other end of lingual mandibular retaining strap 1 as connected to the anterior portion of the lingual side wall of left lower U-shaped member 4 by hole and peg assembly 10a. Clearance 11a corresponds to the prior described clearance 11b.

As also shown in FIGS. 1 and 1a, the oral cavity appliance further includes an upper pair of U-shaped members 12, 13 otherwise referred to as upper pieces, each having buccal and lingual side walls connected by a horizontal portion 23. The right U-shaped member 12 and the left U-shaped members 13 are connected across their lingual side walls by bridge 14. Labial maxillary retaining strap 2 is connected on each of its ends to the buccal side walls of upper U-shaped members 12 and 13. As shown in FIG. 1, labial maxillary retaining strap 2 is connected on one end by hole and peg assembly 15a to the anterior portion of the buccal side wall of left upper U-shaped member 12. The opposite end of lingual mandibular retaining strap 2 is connected to the anterior portion of the buccal side wall of right upper U-shaped member 13 by hole and peg assembly 15b. Clearances 16a, 16b are provided to allow labial maxillary retaining strap 2 to move slightly while maintaining its imbedded level in the labial maxillary tissues and allow for universal fit.

The horizontal portion 23 of upper U-shaped members 12, 13 are provided with ridges complementary to ramped ridges 17. These members also have a keyway complementary to dove-tailed key 18. As such, the lower pair of U-shaped members 4, 7 may be moved forward in relation to the upper pair of U-shaped members 12, 13 resulting in the movement of the mandible into an open and forward position. It should be noted that dove-tailed key 18 is angled so as to allow the lower members 4, 7 to slide forward from said upper members 12, 13 without deforming the alignment of upper members 12, 13.

Upper pair of U-shaped members 12, 13, along with bridge 14 and labial maxillary retaining strap 2 can be said to form in combination an upper piece to Applicant's two-piece appliance. By virtue of the complimentary ridges and keyway present on the horizontal portion 23 of upper members 12, 13, the upper piece of the device is slidably engageable upon the lower piece. There is further provided on the buccal side walls of upper members 12, 13 pointers 19 directed downwardly toward lower members 4, 7. Lower members 4, 7 contain calibration markings 20 such that the user can ensure that the position of upper member 12 in relation to lower member 4 is consistent with the position of upper member 13 to lower member 7.

All hinge assemblies (i.e. hole and peg assemblies 10a–b, 15a–b) are constructed so that their outside surfaces are flush with the side walls of the upper and lower members.

Figure 2:
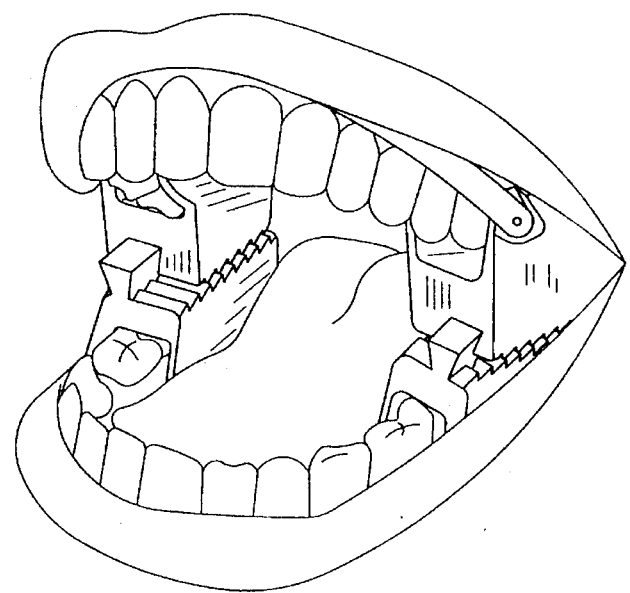
FIG. 2 is a perspective view showing the invention in place with the mouth in an open position and the mandible in a forward position.
Figure 3:
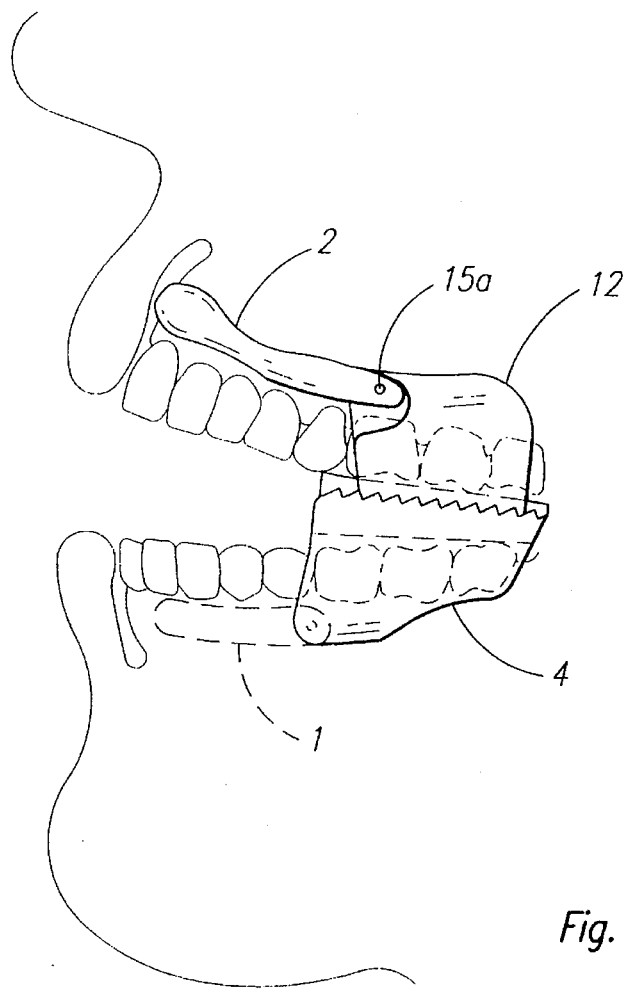
FIG. 3 is a left side view showing the invention in place in the mouth.

Turning now to FIGS. 2 and 3, a perspective view of the preferred embodiment of the invention is shown in place in the mouth with the mandible held in an open and forward position. Lingual mandibular retaining strap 1 is seen to contact and imbed in the lingual mandibular tissues below the mandibular anterior teeth, while labial maxillary retaining strap 2 contacts and imbeds in the labial maxillary tissues above the maxillary anterior teeth.

Figure 4:
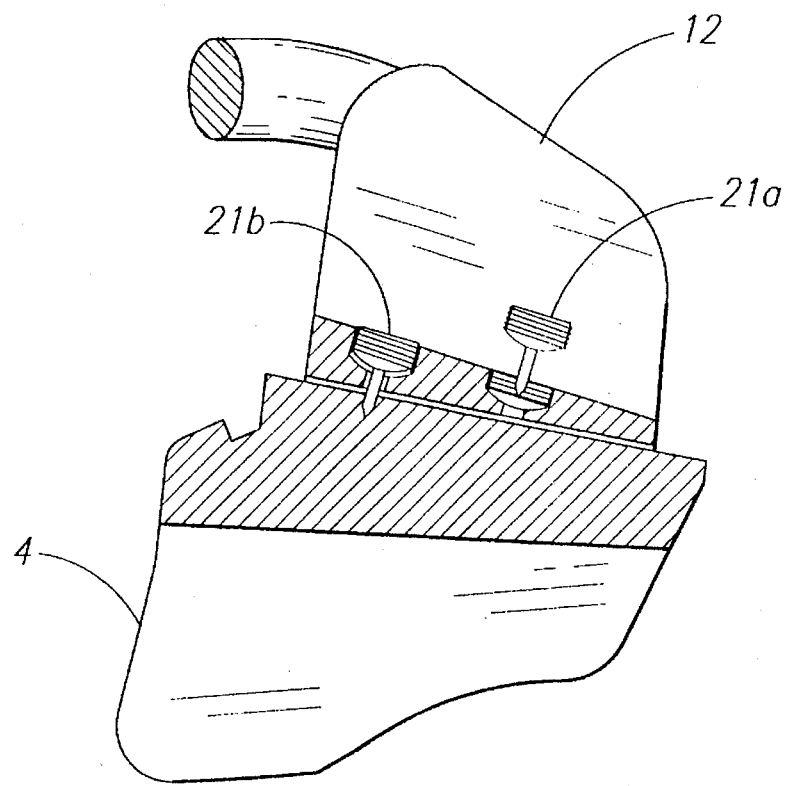

FIG. 4 shows the positioning of two threaded set screws 21a–b which are insertable into complimentary threaded receptacles contained in upper U-shaped member 12. Corresponding structure is also found in upper U-shaped member 13. Using a set screw 21, the user can permanently set the desired adjustment. Preferably, one set screw is tightened down such that a spike sets into dove-tailed key 18. Only one set screw need be tightened on each side, the other being reserved for later adjustments if necessary. Set screws 21a–b may be stainless steel, having complementary stainless steel guides set into the upper members 12, 13. Set screws 21a–b are sharp pointed so when set they pierce through the upper U-shaped members 12, 13 into the corresponding dove-tailed key 18. Each set screw 21 is shouldered for self-stopping at the correct depth of penetration.

Figure 5:
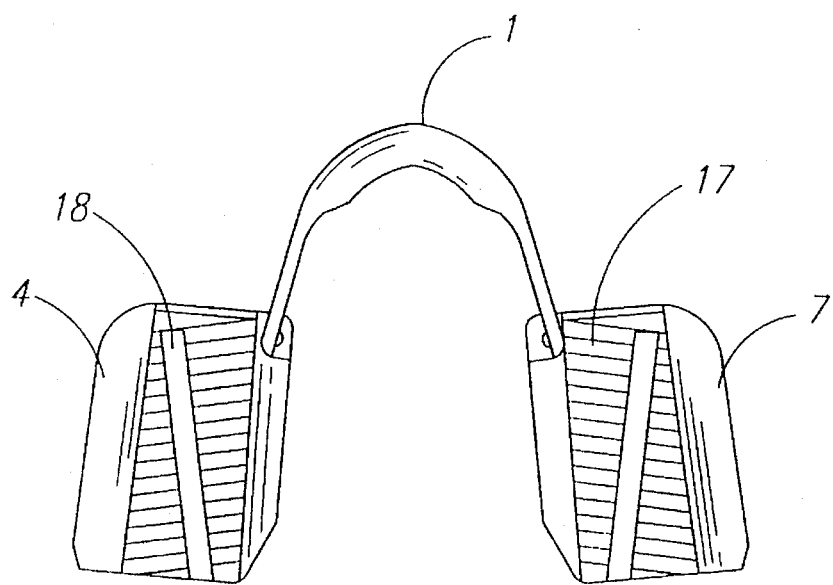
FIG. 5 is a top view of the lower piece of the preferred embodiment of the invention.

The one-way ramped ridges 17 and angled dove-tailed keys 18 of the lower pair of U-shaped members 4, 7 are shown in FIG. 5.

In the preferred embodiment, the oral cavity appliance is made from a thermoplastic material, known in the art, which conforms to the user's particular mouth structure. The user will buy the device over-the-counter and will perform the fitting in the privacy of the home. In the fitting process, the user will first insert the device in the mouth and position the lingual mandibular retaining strap 1 and the labial maxillary retaining strap 2 as needed. The user then uses a trial-by-error method to find the most forward position where snoring is eliminated and no cramping of jaw muscles is experienced. The lower U-shaped members 4, 7 can be adjusted at least 10 mm forward and correspondingly opened to 15 to 20 mm, regardless of whether and what amount the natural position of the user's jaw is protrusive or retrusive. The one-way ramped ridges 17 act to hold the upper and lower members in the adjusted positions until the user is confident that the best adjustment has been found. The user makes certain that the pointers 19 indicate at corresponding lines on each calibration scale 20. Finally, the user tightens one of the set screws 21, but not both, on each of upper U-shaped members 12, 13 to permanently set the adjustment.

As shown in FIGS. 2 and 3, the apparatus functions to maintain the open position of the mouth and the forward position of the mandible without putting stress on the user's teeth. Instead, the pressure is applied directly to the maxilla and mandible through retaining straps 1, 2. This relieves the user of the discomfort associated with prior devices and prevents splaying or repositioning of the teeth.

As also shown in FIGS. 2 and 3, it is apparent that stabilization of the maxilla and mandible in an open position and the affirmation of the mandible in a forward posture occurs by virtue of retaining straps 1, 2. The retaining straps, however, do not prevent all lateral movement of the jaw. Thus, during use the user may, if necessary, give some relief to the muscles of the temporal mandibular joint. This is made easier by the provision of clearances 11*a–b* and 16*a–b*.

In other alternative embodiments, the means for adjusting the forward thrust of the mandible includes other suitable mechanisms, such as a screw-type track mechanism, known in the art, which functions to adjust the spatial relationship of lower U-shaped members 4, 7 to upper U-shaped members 12, 13.

Simple modifications to the present invention will make it effective for use by persons with no natural or prosthetic dentition. An alternate embodiment of the invention designed for persons with no dentition would have a lesser depth of side walls so that the posterior end of the device would fit flush against the user's gums where normally it contacts the mandibular and maxillary molars and bicuspids.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiment set forth herein for purposes of exemplification, but is to be limited only by the scope of the attached claim or claims, including the full range of equivalency to which each element thereof is entitled.

What is claimed is:

1. A universal, user-adjustable oral cavity appliance designed to control snoring and reduce episodes of obstructive sleep apnea by maintaining the mandible in an open and forward position during sleep, said appliance comprising:

a. a lingual mandibular pressure strap means to contact and to embed in the lingual mandibular tissues below the mandibular anterior teeth and to push against the contacted lingual mandibular tissues;

b. a labial maxillary pressure strap means to contact and to embed in the labial maxillary tissues above the maxillary anterior teeth and to pull against the contacted labial maxillary tissues; and c. means for adjustably connecting said straps such that the relative position of each said strap to the other may be varied to obtain a separation between the maxilla and mandible and a forward thrust of the mandible sufficient to prevent occlusion of the oropharyngeal airway.

2. An oral cavity appliance according to claim 1 wherein said pressure straps are of an elliptical cross-section.

3. An oral cavity appliance according to claim 1 wherein said labial maxillary pressure strap is provided with a frenulum notch.

4. An oral cavity appliance according to claim 1 wherein said means for adjustably connecting said straps comprises:

a. a lower pair of U-shaped members, each having one-way, ramped ridges thereon integrated with a dove-tailed key, said lingual mandibular pressure strap being affixed between said lower members, and b. an upper pair of U-shaped members, each having ridges thereon complementary to said ramped ridges and a keyway complementary to said dove-tailed key, said labial maxillary pressure strap being affixed between said upper members, such that the forward movement of said lower members in relation to said upper members works to move the mandible into an open and forward position.

5. An oral cavity appliance according to claim 4 wherein said dove-tailed keys are angled so as to allow said lower members to slide forward from said upper members without deforming the alignment of said upper members.

6. An oral cavity appliance according to claim 4 where said upper members are provided with a plurality of set screws for permanently setting a desired adjustment.

7. An oral cavity appliance according to claim 4 wherein said pressure straps are affixed to said lower and upper members by a plurality of hinges such that said straps may move slightly while maintaining their embedded level and may allow for universal fit.

8. An oral cavity appliance according to claim 7 wherein said hinges comprise hole and peg assemblies.

9. An oral cavity appliance according to claim 7 wherein said hinges are flush in construction with said lower and upper members.

10. A universal, user-adjustable, oral cavity appliance for maintaining the mandible in an open and forward position during sleep, said appliance comprising:

a. a left lower piece and a right lower piece having a lingual mandibular retaining strap affixed therebetween, said lingual mandibular retaining strap adapted to contact and embed in the lingual mandibular tissues below the mandibular anterior teeth and having one-way, ramped ridges disposed thereon integrated with a dove-tailed key, and b. an left upper piece and a right lower piece having a labial maxillary retaining strap affixed therebetween, said lingual mandibular retaining strap adapted to contact and embed in the labial maxillary tissues above the maxillary anterior teeth and having ridges thereon complementary to said ramped ridges and a keyway complementary to said dove-tailed key, such that the forward movement of said left and right lower pieces in relation to said left and right upper pieces works to move the mandible into an open and forward position.

11. An oral cavity appliance according to claim 10 wherein said retaining straps are of an elliptical cross-section.

12. An oral cavity appliance according to claim 10 wherein said labial maxillary retaining strap is provided with a frenulum notch.

13. An oral cavity appliance according to claim 10 wherein said dove-tailed keys are angled so as to allow said lower piece to slide forward from said upper piece without deforming the alignment of said upper piece.

14. An oral cavity appliance according to claim 10 where said upper piece is provided with a plurality of set screws for permanently setting a desired adjustment.

15. An oral cavity appliance according to claim 10 wherein said retaining straps are affixed to said pieces by a plurality of hinges such that said straps may move slightly while maintaining their embedded level and may allow for universal fit.

16. An oral cavity appliance according to claim 15 wherein said hinges comprise hole and peg assemblies.

17. An oral cavity appliance according to claim 15 wherein said hinges are flush in construction with said lower and upper pieces.

18. A universal, user-adjustable oral cavity appliance for maintaining the mandible in an open and forward position during sleep, said appliance comprising:
   a. left and right U-shaped mandibular members, each adapted to extend from and cover the mandibular molars to the mandibular bicuspids and having one-way, ramped ridges disposed thereon integrated with a dove-tailed key;
   b. a lingual mandibular retaining strap adapted to contact and embed in the lingual mandibular tissues below the mandibular anterior teeth, one end of said strap being connected to said left mandibular member and the second end of said strap being connected to said right mandibular member;
   c. left and right U-shaped maxillary members, each adapted to extend from and cover the maxillary molars to the maxillary bicuspids and having ridges thereon complementary to said ramped ridges and a keyway complementary to said dove-tailed key; and
   d. a labial maxillary retaining strap adapted to contact and embed in the labial maxillary tissues above the maxillary anterior teeth, one end of said strap being connected to said left maxillary member and the second end of said strap being connected to said right maxillary member.

19. An oral cavity appliance according to claim 18 wherein said dove-tailed keys are angled so as to allow said mandibular members to slide forward from said maxillary members without deforming the alignment of said maxillary members.

20. An oral cavity appliance according to claim 18 wherein said retaining straps are affixed to said U-shaped members by a plurality of hinges such that said straps may move slightly while maintaining their embedded level and may allow for universal fit.

21. An oral cavity appliance according to claim 18 where said maxillary members are provided with a plurality of set screws for permanently setting a desired adjustment.

22. An oral cavity appliance according to claim 18 wherein said retaining straps are of an elliptical cross-section.

* * * * *